(12) United States Patent
Singh

(10) Patent No.: US 12,597,495 B2
(45) Date of Patent: Apr. 7, 2026

(54) SYSTEM, METHOD, AND APPARATUS FOR AUTOMATING CREATION OF SUBJECTIVE, OBJECTIVE, ASSESSMENT, AND PLAN (SOAP) REPORTS

(71) Applicant: Vinni Kaur Singh, San Jose, CA (US)

(72) Inventor: Vinni Kaur Singh, San Jose, CA (US)

(73) Assignee: SUHAVI.AI, INC., Sunnyvale, CA (US)

( * ) Notice: Subject to any disclaimer, the term of this patent is extended or adjusted under 35 U.S.C. 154(b) by 33 days.

(21) Appl. No.: 18/593,903

(22) Filed: Mar. 2, 2024

(65) Prior Publication Data

US 2024/0296924 A1 Sep. 5, 2024

Related U.S. Application Data

(60) Provisional application No. 63/449,814, filed on Mar. 3, 2023.

(51) Int. Cl.
*G16H 50/30* (2018.01)
*G10L 15/26* (2006.01)
*G16H 10/60* (2018.01)
*G16H 15/00* (2018.01)

(52) U.S. Cl.
CPC ............. *G16H 15/00* (2018.01); *G10L 15/26* (2013.01)

(58) Field of Classification Search
CPC ................................ G16H 15/00; G10L 15/26
See application file for complete search history.

(56) References Cited

U.S. PATENT DOCUMENTS

2018/0308487 A1* 10/2018 Goel ................... G10L 15/1815
2021/0327582 A1* 10/2021 Joshi ..................... G16H 50/20

* cited by examiner

*Primary Examiner* — Maroun P Kanaan
(74) *Attorney, Agent, or Firm* — PATENT CAPITAL GROUP

(57) ABSTRACT

In an example embodiment, a system, a method, and an apparatus are provided that include an application, configured for: creating a subjective, objective, assessment, and plan (SOAP) report, the creation includes: using a voice-to-text converter to turn a free-form verbal conversation with a patient into a text stream, the text stream is enhanced with metadata from a database to create an enhanced text stream that forms a basis for the SOAP report. Other examples can provide that the metadata includes data from a previous SOAP report, and data associated with a prevision visit of the patient. Still other scenarios can provide that the enhanced text stream is sent to a large language model (LLM) to automatically create a practitioner-specific SOAP report. The SOAP report is structured according to a practitioner's specific requirements, and the SOAP report is automatically entered into a patient database for subsequent access.

20 Claims, 8 Drawing Sheets

200

VERBAL CONVERSATION
202

HealthcareProfessional ⟋204

210

Patient

VoiceToTextConverter ⟋206

212

214

ListentoConversation

VerbalResponse

TextStream ⟋208

METADATA ENHANCEMENT
216

222

PatientDatabase ⟋218

GetMetadata

EnhanceTextStream ⟍220

SOAP REPORT CREATION
224

LargeLanguageModel ⟍226

SOAPReport ⟍228

PatientCareSystem ⟍230

9:12          .ıl 📶 🔋

 SOAP Report

Review and sign the report.

Plan

Root Canal Therapy on Tooth #3:
Anesthesia with 1.7 cc 4% articaine with 1:100K
epinephrine UR PSA
Isolation with rubber dam.
Accessed tooth and removed decay. MB, MB2, P, B
canals located.
K files and NiTi files used to remove infected pulp,
cleaned and disinfected using EDTA and 5% NaOCl.
F1/F2 files used to obturate and calamus used to
backfill. Cotton/cavit temporary placed.

Post-Procedure Care:
Medication: Prescribe antibiotics to prevent infection
and ibuprofen to manage post-procedure discomfort.
Instructions for Patient: Provide post-procedure care
instructions, including oral hygiene practices, avoiding
chewing on the treated side until the tooth is restored,
and signs to watch for that may require immediate
attention.

Next visit: build up/crown #3

Add Text Here.

*Jane*

Signature

Jane Doe             DMD

Name                 Title

122345

License

Submit

    SOAP Report

Review and sign the report.  

Subjective

ID:

Sarah Johnson, 26 years old, single, female

Chief Complaint:
- "My tooth broke."

Medical History:
- Anxiety, sinus problems.

Dental History:
- moderately restored, previous dental visit 8 months ago

Add Text Here.

Objective

Radiographic Exam:
- periapically normal, no widening of PDL.

Hard Tissue Exam:
- fractured DO amalgam and distal buccal cusp #19

Periodontal Exam:
- 2-3 mm probing depth with no bone loss circumferentially.

Add Text Here.

Assessment

Dx:
- fractured cusp, full coverage crown indicated.

Add Text Here.

Plan

Crown:
Anesthesia: 1.7 cc 2% lidocaine with 1:100K epinephrine at LL IAN

SYSTEM, METHOD, AND APPARATUS FOR AUTOMATING CREATION OF SUBJECTIVE, OBJECTIVE, ASSESSMENT, AND PLAN (SOAP) REPORTS

CLAIMING PRIORITY TO A PROVISIONAL

This application claims Priority under any and all relevant provisions of 35 U.S.C. to the Provisional Application having Ser. No. 63/449,814, which was filed on Mar. 3, 2023, and which is hereby incorporated by reference in its entirety.

TECHNICAL FIELD

This disclosure relates in general to the field of healthcare data and, more particularly, to a system, method, and apparatus for automating creation of subjective, objective, assessment, and plan (SOAP) reports.

BACKGROUND

There is increasing pressure on physicians to be both expedient and accurate in their reporting for their clientele/patients. Any collected patient information should be organized, unambiguous, and adhere to specific reporting guidelines. The Subjective, Objective, Assessment and Plan (SOAP) note is an acronym representing a widely used method of documentation to be used by healthcare providers. The SOAP note is a way for healthcare workers to document data exchanges in a structured and organized way. This widely adopted structural SOAP note was theorized almost fifty (50) years ago. It reminds clinicians of specific tasks, while providing a framework for evaluating information. It also provides a cognitive framework for clinical reasoning. The SOAP note helps guide healthcare workers to use their clinical reasoning to assess, diagnose, and treat a patient based on the information provided by them. SOAP notes are an essential piece of information about the health status of the patient as well as a communication document between health professionals. The structure of documentation is a checklist that serves as a cognitive aid and a potential index to retrieve information for learning from the record.

Hence, in many fields of healthcare, there is an obligation for professionals (e.g., dentists, physicians, therapists, counselors, coaching professionals, etc.) to create SOAP reports for their patients. These reports can contain important information about the patient's medical history, current conditions, and possible treatment plans. However, creating these reports can be time-consuming, prone to errors, and may also require significant manual effort. The $21^{st}$ century allows for little time for these healthcare professionals to spend on these critical reporting endeavors.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

2

Figure 3:
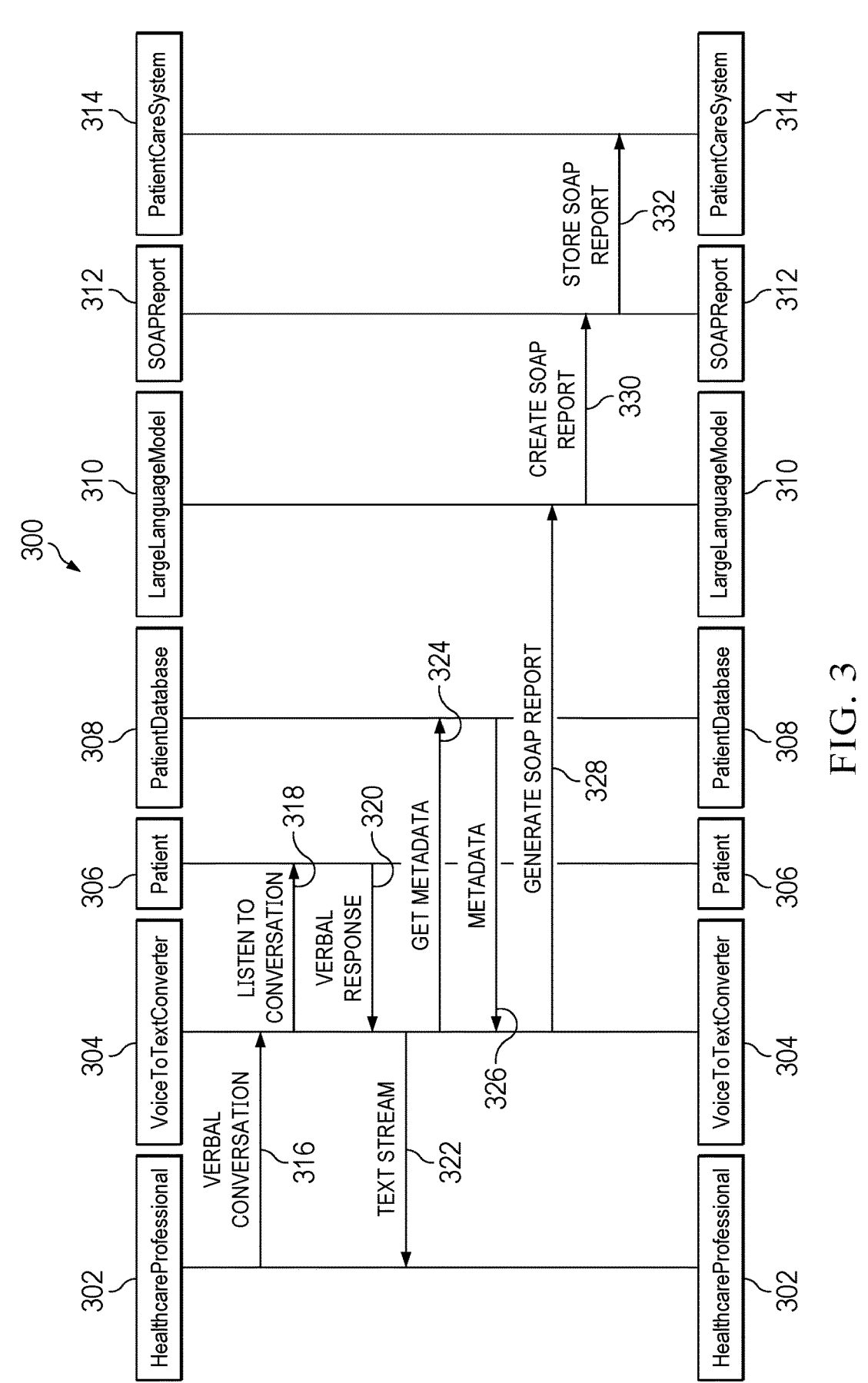
Figure 7:
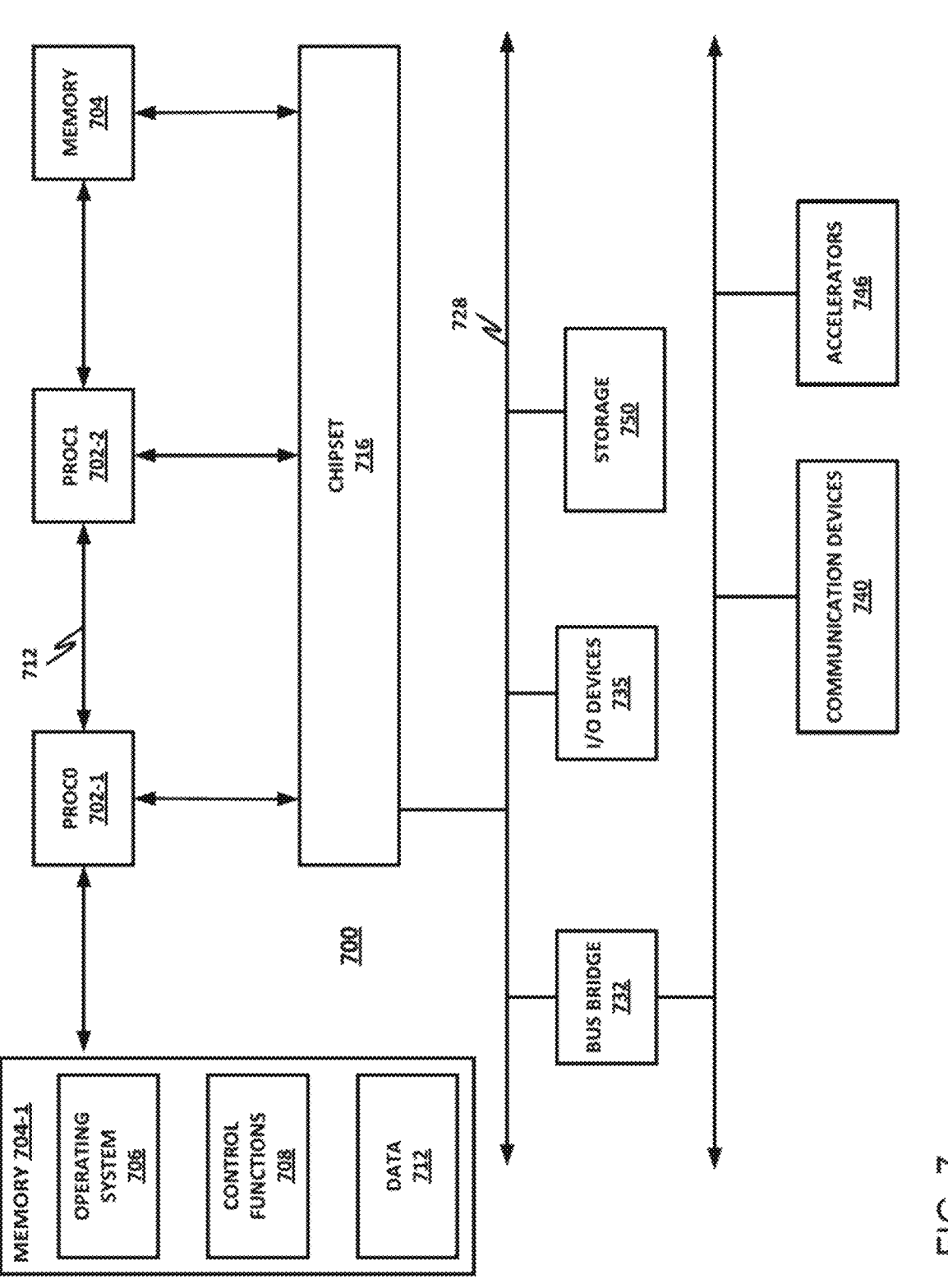

FIG. 3 is a flow diagram illustrating yet another example of a possible interaction involving a patient and a healthcare professional;

FIGS. 4-6B are simplified screenshots illustrating one possible implementation of the present disclosure involving a computer or a smartphone; and FIG. 7 is a simplified block diagram illustrating one possible software and/or hardware platform that can be deployed to achieve the teachings of the present disclosure.

DETAILED DESCRIPTION OF EXAMPLE EMBODIMENTS

Overview of One or More Aspects of Invention

In an example embodiment, a system, method, and apparatus are provided for automating the creation of SOAP reports for healthcare professionals. The system can use a voice-to-text converter to turn a free-form verbal conversation with a patient into a text stream. The text stream can then be enhanced with metadata from a patient's database, including previous SOAP reports, issues noted in previous visits, and other relevant information (some of which may be proprietary or specialized by a given provider or practice). The enhanced text stream can then be fed into a large language model to automatically create a practitioner-specific SOAP report, which can be entered into a patient care database, or any other suitable repository.

The SOAP report is structured according to the practitioner's specific requirements and that can include any relevant information from the text stream, such as the patient's medical history, current condition, and treatment plan. Once the SOAP report is created, it can be automatically entered into the patient care database, where it can be accessed by a healthcare professional, an insurance provider, and/or other authorized personnel.

The present invention provides several advantages and benefits, including: time savings—the automated system reduces the time required to create SOAP reports, freeing healthcare professionals to focus on other tasks; consistency—the automated system ensures that SOAP reports are consistent and structured according to the practitioner's requirements; accuracy—the natural language processing algorithms and machine learning algorithms used in the system ensure that the SOAP reports are accurate and free from errors; enhanced patient care—the automated system provides healthcare professionals with a more complete picture of the patient's medical history, current condition, and treatment plan, enabling them to provide more effective care.

In addition to the features described above, the present invention includes the following unique features and functions:

Real-time voice-to-text conversion: The system uses a voice-to-text converter to convert the free-form verbal conversation with a patient into a text stream in real time, providing immediate access to the information contained in the conversation.

Metadata enhancement: The system enhances the text stream with metadata from the patient's database, including previous SOAP reports and other relevant information, providing a more complete picture of the patient's medical history and condition.

Large language model: The system uses a large language model to automatically create practitioner-specific SOAP reports, which can be customized according to the practitioner's requirements.

Embodiments of the present invention have potential applications and uses in a variety of healthcare settings, including dental practices, medical offices, hospitals, therapy clinics, counseling centers, and coaching services. Hence, the architecture can be used by virtually any healthcare professionals who need to create SOAP reports for their patients, including, but not limited to, dentists, physicians, nurses, therapists, counselors, coaches, teachers, law enforcement professionals, etc. Use cases for the present invention are significant, given the widespread need for SOAP reports in the healthcare industry. The global healthcare IT market is expected to grow from $141 billion in 2020 to $270 billion by 2026, driven in part by the increasing adoption of digital health technologies. The present invention addresses a key pain point for healthcare professionals and has the potential to significantly reduce the time and effort required to create routine SOAP reports and, thereby, improving the efficiency and effectiveness of patient care.

Note that there could be regulatory and bureaucratic challenges and risks associated with certain aspects of the present disclosure. They can include, but are not limited to:

Data privacy and security, as the system should comply with relevant regulations and standards for data privacy and security (e.g., HIPAA in the United States).

Technical challenges, as the system relies on several complex technologies, including natural language processing, artificial intelligence, and machine learning, which may require significant expertise to implement and maintain.

User adoption because healthcare professionals may be resistant to adopting new technologies, particularly if they require significant changes to their workflows or processes.

Overview of Example Flows, Structures and Architectures of the Present Disclosure SOAP notes are commonly found in electronic medical records (EMR) and are used by providers of various backgrounds. Generally, SOAP notes are used as a template to guide the information that physicians add to a patient's EMR. Prehospital care providers, such as emergency medical technicians, may use the same format to communicate patient information to emergency department clinicians. Due to its clear objectives, the SOAP note provides physicians with a way to standardize the organization of a patient's information to reduce confusion when various healthcare professionals see patients. Many healthcare providers, ranging from physicians to behavioral healthcare professionals to veterinarians, use the SOAP note format for their patient's initial visit and to monitor progress during follow-up care.

The four headings of a SOAP note are Subjective, Objective, Assessment and Plan. Each heading is described below.

Subjective

This is the first heading of the SOAP note. Documentation under this heading comes from the "subjective" experiences, personal views or feelings of a patient or someone close to them. In the inpatient setting, interim information is included here. This section provides context for the Assessment and Plan.

Chief Complaint (CC)

The CC or presenting problem is reported by the patient. This can be a symptom, condition, previous diagnosis, or another short statement that describes why the patient is presenting today. The CC is similar to the title of a paper, allowing the reader to get a sense of what the rest of the document will entail.

Examples: chest pain, decreased appetite, shortness of breath.

However, a patient may have multiple CC's, and their first complaint may not be the most significant one. Thus, physicians should encourage patients to state all of their problems, while paying attention to detail to discover the most compelling problem. Identifying the main problem should occur to perform effective and efficient diagnosis.

History of Present Illness (HPI)

The HPI begins with a simple one-line opening statement including the patient's age, sex, and reason for the visit.

Example: 47-year-old female presenting with abdominal pain.

This is the section where the patient can elaborate on their chief complaint. An acronym often used to organize the HPI is termed "OLDCARTS":

Onset: When did the CC begin?

Location: Where is the CC located?

Duration: How long has the CC been going on for?

Characterization: How does the patient describe the CC?

Alleviating and Aggravating factors: What makes the CC better? Worse?

Radiation: Does the CC move or stay in one location?

Temporal factor: Is the CC worse (or better) at a certain time of the day?

Severity: Using a scale of 1 to 10, 1 being the least, 10 being the worst, how does the patient rate the CC?

It is important for clinicians to focus on the quality and clarity of their patient's notes, rather than include excessive detail.

History

Medical history: Pertinent current or past medical conditions

Surgical history: Try to include the year of the surgery and surgeon if possible.

Family history: Include pertinent family history. Avoid documenting the medical history of every person in the patient's family.

Social History: An acronym that may be used here is HEADSS which stands for Home and Environment; Education, Employment, Eating; Activities; Drugs; Sexuality; and Suicide/Depression.

Review of Systems (ROS)

This is a system-based list of questions that help uncover symptoms not otherwise mentioned by the patient.

General: Weight loss, decreased appetite

Gastrointestinal: Abdominal pain, hematochezia

Musculoskeletal: Toe pain, decreased right shoulder range of motion

Current Medications, Allergies

Current medications and allergies may be listed under the Subjective or Objective sections. However, it is important that with any medication documented, to include the medication name, dose, route, and how often.

Example: Motrin 600 mg orally every 4 to 6 hours for 5 days

Objective

This section documents the objective data from the patient encounter. This includes:

Vital signs

Physical exam findings

Laboratory data

Imaging results

Other diagnostic data

Recognition and review of the documentation of other clinicians.

A common mistake is distinguishing between symptoms and signs. Symptoms are the patient's subjective description and should be documented under the subjective heading, while a sign is an objective finding related to the associated symptom reported by the patient. An example of this is a patient stating he has "stomach pain," which is a symptom, documented under the subjective heading. Versus "abdominal tenderness to palpation," an objective sign documented under the objective heading.

Assessment

This section documents the synthesis of "subjective" and "objective" evidence to arrive at a diagnosis. This is the assessment of the patient's status through analysis of the problem, possible interaction of the problems, and changes in the status of the problems. Elements include the following.

Problem

List the problem list in order of importance. A problem is often known as a diagnosis.

Differential Diagnosis

This is a list of the different possible diagnoses, from most to least likely, and the thought process behind this list. This is where the decision-making process is explained in depth. Included should be the possibility of other diagnoses that may harm the patient, but are less likely.

Example: Problem 1, Differential Diagnoses, Discussion, Plan for problem 1 (described in the plan below). Repeat for additional problems.

Plan

This section details the need for additional testing and consultation with other clinicians to address the patient's illnesses. It also addresses any additional steps being taken to treat the patient. This section helps future physicians understand what needs to be done next. For each problem:

State which testing is needed and the rationale for choosing each test to resolve diagnostic ambiguities; ideally what the next step would be if positive or negative.

Therapy needed (medications)

Specialist referral(s) or consults

Patient education, counseling

A comprehensive SOAP note has to consider subjective and objective information, and accurately assess it to create the patient-specific assessment and plan.

The following information illustrates an example exchange that can be captured using the SOAP report format and the teachings of the present disclosure.

Subjective:

Chief complaint: Broken tooth causing pain.

History of present illness: Patient reports tooth pain that began two days ago, located in the upper left quadrant of the mouth, and described as sharp and constant. Patient has a history of cavities and has not been to a dentist in the past two years.

Additional symptoms: Patient reports anxiety, but no other symptoms mentioned.

Objective:

Vital signs: Blood pressure taken three minutes prior to the appointment is 104/80, pulse 117. Blood pressure taken later during the appointment is 102/79, pulse 102.

Oral examination: Examination reveals a broken tooth in the upper left quadrant of the mouth, mild gum inflammation.

Radiographic examination: No radiographic examination mentioned.

Assessment:

Diagnoses: Broken tooth, mild gingivitis

Treatment plan: Tooth extraction, cleaning.

Plan:

Procedures: Tooth extraction and cleaning

Medications: None mentioned

Follow-up: Patient will return for a follow-up appointment in 3 months. Instructions for post-operative care will be given after the procedure.

By way of example, consider the following doctor-patient exchange in conjunction with the ensuing FIGURES.

Example Doctor/Patient Exchange

Doctor 0:00

Hi, Patient Name, how are you? I'm good. Okay, so today we're going to be taking out that top broken tooth. Okay. Do you have any questions about that? No questions. And then looks like your blood pressures 104 over 80 Pulse 117 a little high on the pulse. So, what we're going to do before I get you numb, is we're going to check your blood pressure again. When was that taken? Very Doctor 0:31

How long ago?

Doctor 0:34

Three minutes. Okay, so let's Okay, I want you to just kind of rest and relax for a few minutes. Did we take it over her sweatshirt? Or did we take the blood pressure? Over the sweatshirt? Yeah. Can you take out your arm on the other arm that you didn't do? So just take off the arm. That's fine. You've got the blanket; you can use that. No one else is here. So, we'll just cover you up. Okay, and then and then just relax for a few. And then we'll go ahead. Do you normally have anxiety, or just today, just in general. Okay, no worries, but I just want to make sure your your pulse on sounds is quite high. So, your blood pressure looks good, but your pulse your heart's kind of racing here. So, I'll be back with you in a few minutes okay?

Doctor 1:38

All right, Patient Name, so I'm going to your blood pressure came to 102 over 79 pulse. 102. So it came down that's great. Let's go ahead and get you numb. Now. You feel it. All right. Feel a little better. Yeah, so anxious. That's, that's understandable. But your your blood pressure is looking better. So, let's go ahead and get you know, I'm okay. You're going to take a deep breath for me. Good. And then what you're going to do is lift your chin up for me. Relax your lips. Deep breath.

Doctor 2:19

Breathe.

Doctor 2:19

Hold still for me. There you go. You're going to get some tapping on your shoulder. Okay.

Doctor 2:24

You're right there service.

Doctor 2:36 era planar, they're booked up. Okay, there's

Doctor 2:41 going to be a little bit more but you're not going to feel this one. Okay, you're going to feel more a little bit more tapping. On your shoulder. So actually live.

Doctor 3:01 open really big three big stretch extract. You might feel a little pressure here. Okay. Breathe.

Doctor 3:13

Deep breathing

Doctor 3:20

Breathe. Breathe. I know that was a tough one. Breathe.

Doctor 3:47

We're going to leave for you to get numb and then we'll get started. Okay, very deep breaths. Okay, all right. All right, we're going to do is check the numbing and see how you're doing and then we'll get started. Okay.

Doctor 4:04

So, you're going to feel a lot of pushing.

Doctor 4:07 and a lot of pressure, okay

Doctor 4:16

That's normal, okay to feel that chin up all the way. All the way up data and then open up as big as you can. Good job. So, a lot of pushing Okay. Deep breath breathing Doctor 4:54

All right let's see how that's doing.

Doctor 5:02

Again, you're going to feel a lot of pushing and a lot of pressure. Okay, I'm going to need you to tilt your head back and take deep breaths okay?

Doctor 5:25 push you towards the side. I want you to push me about what.

Doctor 5:58

You're doing great.

Doctor 6:09

Okay, it's an odd spot to apply pressure. So let me see if I have to manually do it open, I should know that works. Let's try that. Push hard. Okay, I want you just to relax for a couple minutes. And then we'll go over your instructions with you, okay. You feel all right. I know that was a lot of pressure.

Doctor 6:34

You survived.

Doctor 6:36

And you did great. It was a very odd position. So, you know it's a little bit more challenging technically to take it out because it's had an odd spot but we're able to do it and the whole thing came out in one piece. So, no problems. Now. We'll get a better idea about that neighboring tooth. Now that that this other broken tooth is not in the way as to how to how to tackle that. Are you establishing your care with our office in terms of like your ongoing care your routine exams and checkups, cleanings, and all that?

Doctor 7:17

You're getting the membership, you said okay.

Doctor 7:29

For the for the next 24 hours at least I don't want you playing with your tongue with the wound. Okay, so don't disturb the wounds. You might feel you're definitely going to feel like there's a hole there which there is right. I just want you to not to try to play with it. Okay. And then when you eat you're going to want to eat up the side of your mouth. The left side of your mouth, okay? Nope. Do you smoke? Okay, so no smoking, brushing, you can brush your teeth, but I wouldn't brush your teeth today. So, start brushing tomorrow. Gently brush your teeth. Don't even brush the wound. Okay, just brush your teeth. Starting tomorrow. Today. You don't have to pay, avoid mouth rinsing for one day. Okay, everything I'm telling you is on the paper, so you don't have to remember everything. I'm just going over it so that you hear it twice. You don't want to rinse your mouth today. You're going to start rinsing gently tomorrow. Okay, so what you're going to do when you rinse is you're going to put the water in your mouth or the water in your mouth and you're just kind of move your head back and forth rather than swishing. Okay, good to swish. The clock can come out, so I want you just to kind of use gravity, shake your head and move it around. And then when you open, I don't want you spinning. I want you to open your mouth and let it fall out or what no no not mouthwash water yeah.

Doctor 9:05

Figure 1:
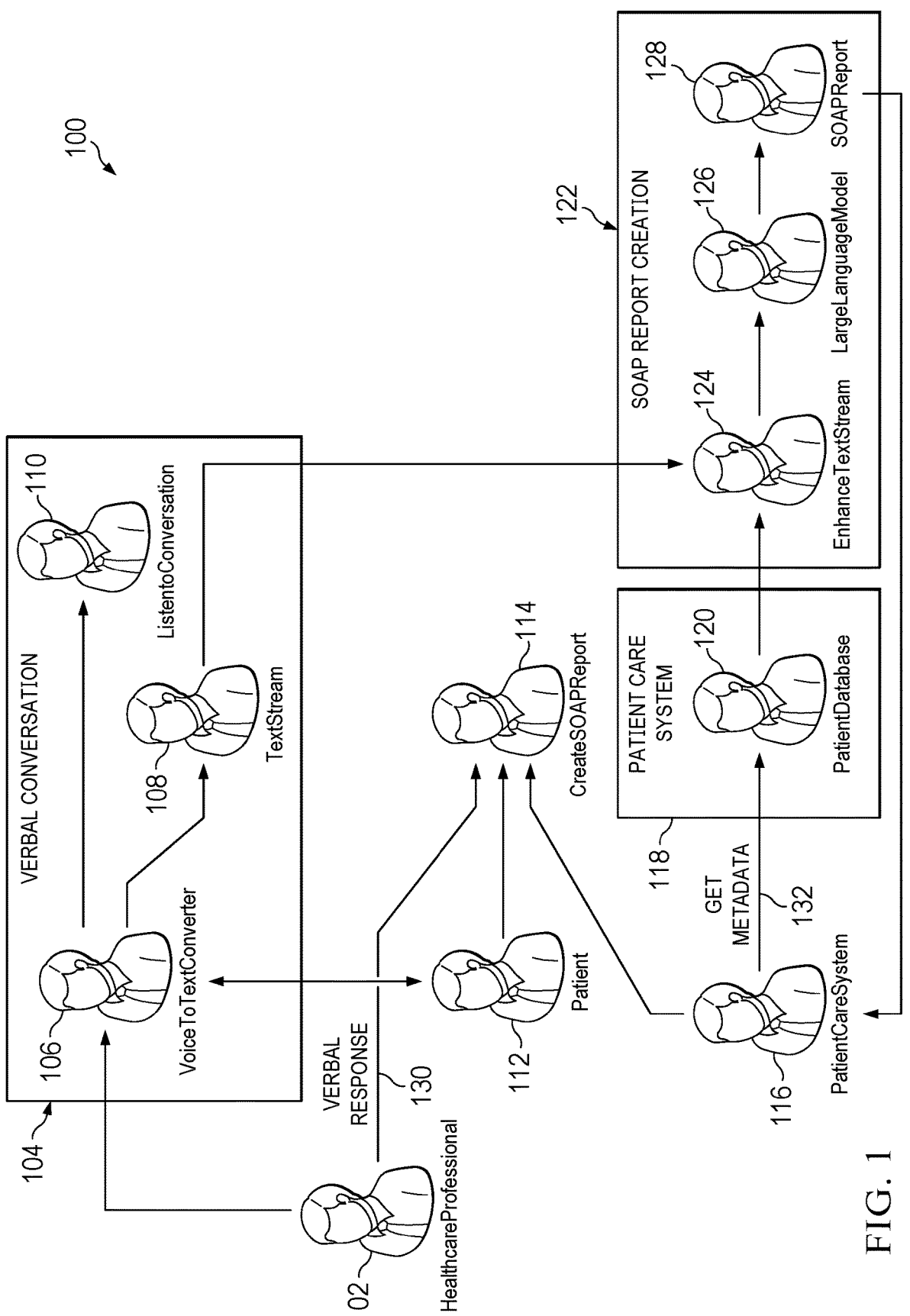
FIG. 1 is a simplified block diagram illustrating example aspects of a possible architecture of the present disclosure.

Okay, so I wrote that on here, mouthwash is water but no mouthwash like blistering or something. Hey. You can use warm saltwater, as well. Okay, so warm saltwater is a nice sort of natural antibiotic. So, what it does is you take a cup of water, like an eight-ounce glass of water you put a teaspoon of salt so should be really salty. Warm it up. And gently swish with that again, back, and forth. No vigorous swishing. Okay. And then again, let it fall out. No spitting out, okay. You can eat regular meals. You want to avoid anything really, really spicy, or hot though. You can scan this QR code. There's a list of foods and all the instructions I'm giving you are also on there. So, if you get one week in one week, okay, and then bleeding is normal and you can change out your own gauze you probably after probably before you when you leave today it's probably already clotted, but if you feel some losing that's normal. But if for some reason it is and you're just not able to make a stop call me or go to the emergency room. Okay. Otherwise, a little bit of oozing is normal. So that's expected even after it's got sort of bleeding with a gauze you may still get some oozing. Okay, for up to one day, so this time tomorrow, okay. You probably won't need more than just some Advil, okay? Because it helps with the inflammation that was caused, alternate Advil and Tylenol. So, if you want to take Advil, okay, and then lastly, I don't think you'll need it but if you have any swelling, you can apply an ice pack to your face. Okay. 20 minutes on 20 hours off, repeat multiple times a day. I mean, I don't know what your hours are. But you're probably good to go back to that in terms of your physical condition. You're okay to go back to work today if you need to. Otherwise, you can go back tomorrow. No, you're going to we're going to take out the gauze. I'm going to have Mary dress, put another dressing in and then just check the bleeding. I'll be right back. Okay, Mary Returning back to the FIGURES, FIG. 1 is a simplified block diagram illustrating example aspects of one possible architecture/configuration of the present disclosure. In one example, system 100 includes a healthcare professional 102 and a patient 112, where the other symbols are illustrating how the information is traveling and/or being processed until it reaches a next stage or a final result. A patient database 120 is provided, which is coupled to the patient care system 116, where metadata retrieval is being conducted. The system 100 includes a patient care system 118, a SOAP report creation piece 122, a large language model (LLM) 126, a SOAP report 128, an enhance text stream component 124, a create SOAP report component 114, a verbal response 130, a text stream 108, a listen to conversation component 110, and a verbal conversation component 104. A voice-to-text converter 106 is provided along with an enhancer for the text stream. Metadata is obtained during activities involving data collection. A series of arrows are illustrated to demonstrate the interaction between components of the architecture.

Figure 2:
FIG. 2 is a flowchart that illustrates an example progression from a verbal conversation involving a healthcare professional and a patient that is processed in the architecture.

FIG. 2 is a flowchart that illustrates the progression from a verbal conversation involving a healthcare profession and a patient to a voice-to-text converter, then to a metadata enhancement, which then results in a SOAP report creation.

In one non-limiting example flow, a healthcare professional would initiate an exchange with a patient, and then subsequent steps would ensue as indicated. FIG. 2 includes similar elements to that described with reference to FIG. 1, where these elements can cooperate together to achieve the capabilities discussed herein. In this non-limiting example, a system 200 includes a verbal conversation 202, a healthcare professional 204 (e.g., a dentist), a voice to text converter 206, a text stream 208, a patient 210, a listen to conversation component 212, a verbal response 214, a metadata enhancement 216, a patient database 218, an enhance text stream 220, a get metadata component 222, a SOAP report creation 224, a large language model 226, a SOAP report 228, and a patient care system 230.

FIG. 3 is a flow diagram illustrating yet another example of a possible interaction involving a patient and a healthcare provider. In this example, the flow diagram indicates a series of steps and processes to highlight some of the possible teachings of the present disclosure. FIG. 3 includes a system 300 that further includes a healthcare professional 302, a voice to text converter 304, a patient 306, a patient database 308, an LLM, a SOAP report 312, a patient care system 314, a verbal conversation 316, a listen to conversation component 318, a verbal response 320, a text stream 322, a metadata component 324, a metadata 326, a generate SOAP report component 328, a create SOAP report 330, and a store SOAP report component 332.

Note the present disclosure overcomes a number of shortcomings in current technologies that seek to assist in medical dictation, report generation, etc. For example, simplistic text to voice systems (e.g., DragonSpeak software) cannot integrate into the practice management systems to automatically bring in the targeted metadata about an appointment, a patient, the relevant history of the patient, the procedure details, the proprietary information for the practitioner and/ or the practice, etc. By contrast, the architecture of the present disclosure provides the ability to connect a set of application program interfaces (APIs) to the speech software and also provides a direct conduit such that it becomes visible to a server, instead of simply having a rudimentary recording stored on a smartphone. In addition, superfluous dialogue (simple chatting not relevant to what would ultimately be reported on a chart) can be minimized, eliminated, or intentionally ignored during the capture of the appointment data. This could be provided as a setting in the system that could allow, for example, a single line summarizing "patient has just returned from a vacation in Hawaii" or "patient has just lost his mother" without having a blunt speech-to-text capture of an entire conversation that would be irrelevant to the patient's appointment or care. The system is intuitive, employing machine-learning and/or AI technology, to discover and understand which data is most significant for capture. The practitioners' notes, settings, ultimate writeups, etc. can be fed back into the system for better accuracy for future reporting.

FIGS. 4-6B are simplified screenshots illustrating one possible implementation of the present disclosure. In operation, once the Application is downloaded from an App Store, a website, etc., then the user can register herself or her practice (using a suitable ID/password). After a suitable authentication, the user grants the application access to her practice management systems or to other databases of the practice. This allows the application to retrieve data for further processing and/or storage (e.g., in the cloud). Once permissions have been resolved and the data accessed, the application can begin showing the calendar/appointments, as indicated in the screenshots. A practitioner can simply navigate through her daily practice, pressing start as an appointment begins for any given patient. At the end of the work day (or at any other suitable time interval), the practitioner can review the collected information, execute signatures for the generated charts, and/or make any additional comments, edits, additions to the collected/processed information. Additionally, the application can be used as a liaison between the practice/practitioner and insurance companies or any other 3$^{rd}$ party provider. This can include adjudicating insurance claims, submitting claims for payment, submitting information to government agencies, resolving invoicing issues generally, etc. Stated in different terms, the application can help facilitate and expedite adjudication of claims to pay dentists. In current systems, a human has to read the text associated with the claim, whereas the architecture disclosed herein is able to understand context for why a treatment is being rendered. For example, the application can determine whether it makes sense with the x-rays and text provided to pay a given claim. This ability can eliminate a human from having to process an associated claim.

Additionally, while the architecture can use default settings for a given practice, it is customizable to account for any specialties or proprietary data of the practitioner or the practice (unique procedures to the practitioner or the practice, cultural differences, special acronyms, internal codes, etc.).

Returning to FIG. 4 and the ensuing screenshots associated with an example dental appointment, these illustrations collectively reflect potential prompts that can be sent to a language model, along with the appointment details, the transcript, and the technical dental procedure for the appointment. Note that in these examples, prompts are also provided to the practitioner using the application, but these should not limit in any way the broad scope of the present disclosure. Such suggestions are only being used for teaching purposes and, therefore, should be construed as such.

Figure 4:
Figure 6A:
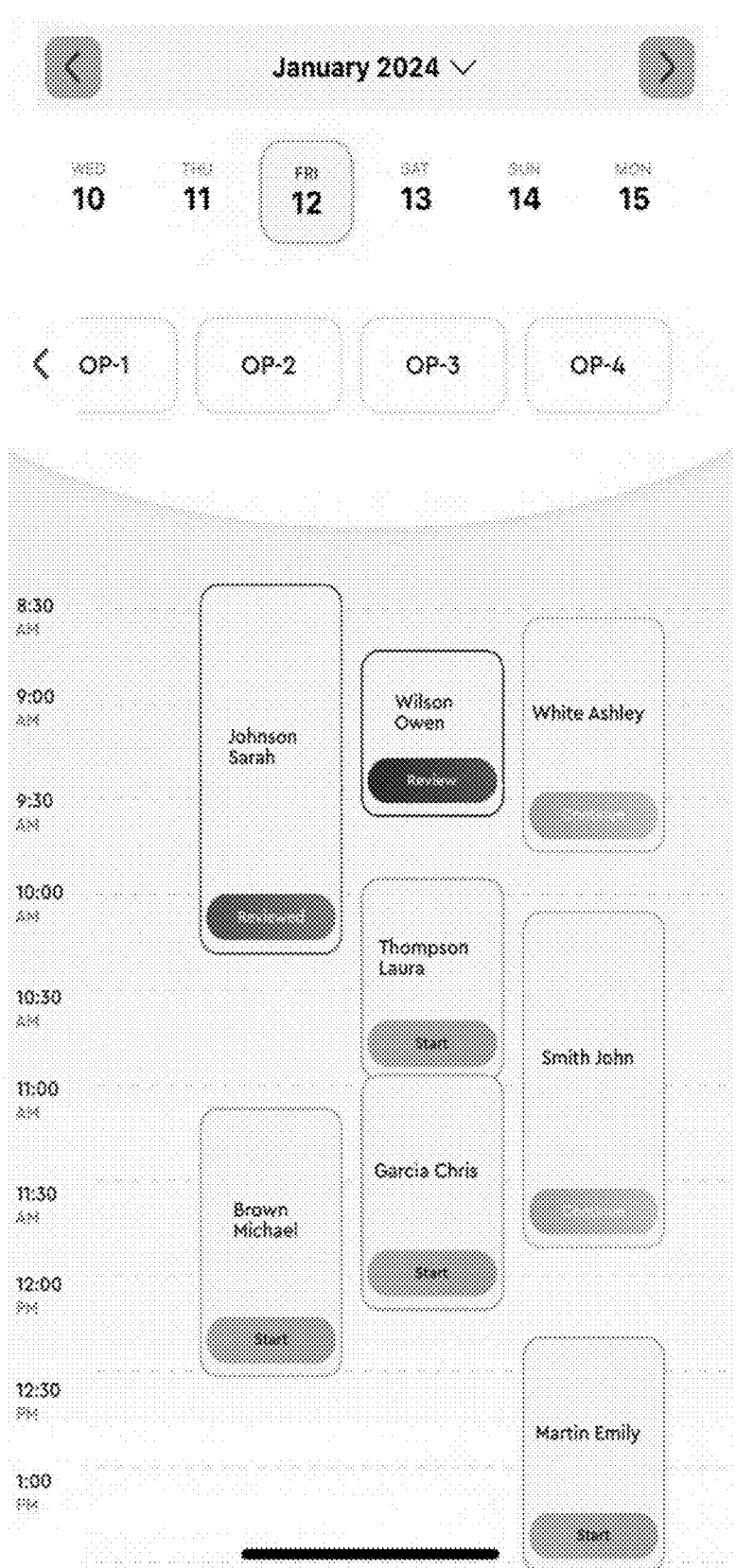

In the example beginning in FIG. 4, this is the English description that then can be turned into jason/JavaScript and API calls to, for example, be provided to an LLM. Provided here is one strategy behind the generation of the SOAP note. In this example, the report is generated in sections, meaning there will be three API submissions, each submission asking for the S, O and A parts, respectively.

The technical dental procedure steps (example in the end) for the appointment are used to enhance the O and A parts. Hence, a voice-to-text converter is used to turn a free-form verbal conversation with a patient into a text stream, where the text stream is enhanced with metadata from any suitable database to create an enhanced text stream that forms a basis for the SOAP report. The Objective portion and the Assessment portion of the SOAP report can be suitably enhanced in creating the resulting SOAP report.

Instructions and format are in one block followed by the appointment metadata, the transcript, and then followed by the technical details of the dental procedures.

########

DentScribe SOAPgenAI is designed for creating SOAP notes from dental appointment transcripts with precision. From the prompt input, if a Detailed Plan (P) part is provided, the application uses the relevant information in the user-provided Plan to fill in details for the Objective (O) and Assessment (A) parts of the SOAP note.

The application then uses shorthand notation for teeth (e.g., '#4' for tooth number four) in the appropriate sections of the report. The application maintains a professional and formal tone, ensuring clarity, conciseness, and alignment with medical documentation standards. One crucial aspect is the accuracy of the citations—they should be exact quotes from the transcript, not paraphrased or summarized in this example. If the practitioner uses the information from the user-provided Plan for the O and A sections of the SOAP note, mark those with a prefix "FromUserPlan:"

Produce the SOAP note by strictly adhering to the following template:

Subjective (S):

[For each of the following subsections thoroughly analyze the transcript and fill in the details]

ID: [Patient Identifying Information]

Chief Complaint: [Main issue described by the patient, or "None" if applicable.

Medical History: [Relevant medical issues, or "None" if medical history is not discussed]

Dental History: [Summarized dental history in 1 line or "None" if no dental history]

Allergies: [List any allergies, or "None" if no known drug allergies]

Social History: [Brief mention of patient's social background in one line or "None" if no social history is discussed]

Citations: ['Citations:' are mandatory for the Subjective findings reported above. They can be presented here but not in the subsections above. This can ensure that there is no false reporting on the practitioner's part and that everything reported in the Subjective section above is factual. This citations subsection should contain direct, verbatim quotes from the provided transcript, alongside the specific line number. For example, if a patient mentions a recent sporting event, include the exact phrase and state "Went to see a basketball game [line #X]." The same is indicated for the doctor. Attribute direct quotations from the doctor as evidence. This ensures transparency and accuracy, aligning the SOAP note closely with the actual transcript.]

Objective (O):

[For each of the following subsections thoroughly analyze the transcript and fill in the details]

Intraoral/Extraoral Findings: [Findings, or "No significant findings" if none]

TMJ: [TMJ findings, or "Normal" if none]

Radiographic Exam: [Findings, or "No significant findings" if none]

Hard Tissue Exam: [Findings, or "No significant findings" if none. Use shorthand notation for teeth (e.g., '#4' for tooth number four).]

Periodontal Exam: [Findings, or "No significant findings" if none]

Orthodontic Exam: [Findings, or "Class I Occlusion" if none]

Other objective findings: [Findings or "None" ]

Citations: ['Citations' are mandatory for all the Objective findings reported above. They are to be presented here and not in the subsections above. This will ensure that there is no false reporting on the practitioner's part and that everything reported in the Objective section is factual. This citations subsection should contain direct, verbatim quotes from the provided transcript, alongside the specific line number. Attribute direct quotations from the doctor as evidence. This ensures transparency and accuracy, aligning the SOAP note closely with the actual transcript.]

Assessment (A):

Diagnosis and Prognosis: [Diagnosis and prognosis based on subjective and objective information. If relevant Use shorthand notation for teeth (e.g., '#31' for tooth number 31).]

Citations: [For each section, a 'Citations:' subsection is mandatory. This subsection should contain direct, verbatim quotes from the provided transcript, alongside the specific line number. Attribute direct quotations from the doctor as evidence. This ensures transparency and accuracy, aligning the SOAP note closely with the actual transcript.

Plan (P):

[Treatment plan, including treatments, patient education, follow-up schedules, and preventive measures]

Make a second pass on the transcript and check if there is any missing information in the SOAP note and fill in any missing details. It is more important to be accurate and not miss any information than to be fast.

########

Example Technical Dental Procedure

D2330—Resin-based composite—one surface, anterior
Anesthesia:

Administered 1.7 cc 2% lidocaine with 1:100K epinephrine at LOCATION, 1.7 cc 3% citanest plain at LOCATION, 1.7 cc 4% articaine with 1:100K epinephrine at LOCATIONTreatment:

Isovac isolation used.

Removed all decay.

Garrison matrix/ring/wedge placed.

Very deep decay #

No frank pulp exposure, liner placed.

Selective enamel etched with 37% phosphoric acid etch for 15 s.

Bond with Scotchbond universal scrubbed into tooth for 20 s.

Light cured for 20 s.

SDR flowable placed as dentin layer.

Filtek composite placed incrementally and cured in between increments.

Finished, polished, checked, and adjusted occlusion as needed.

Contacts flossed.

Postoperative instructions given to the patient. Informed the patient that due to the deep filling, they may experience discomfort or may need root canal treatment (RCT). Advised the patient to return to the office if needed.

The patient left in excellent spirits.

Note that one feature of the present invention includes a subscription model that may include users (e.g., practitioners) paying for access to use the app. or the associated software for performing one or more of the activities discussed herein. For example, a server can be operable to disable and/or enable certain functions and modes of application and/or services of the architecture of the present disclosure. The server can configure all practitioners' devices (computers, smartphones, etc.) or a group of users in a practice such that all corresponding devices used by a particular business entity are configured with the same functionality. If the user or practice is delinquent in subscription payments, devices may have their associated SOAP application disabled completely and/or access to certain functions may be blocked.

FIG. 7 is a block diagram of a software and/or hardware platform 700 to be used in creating intelligent SOAP reports in accordance with one example embodiment of the present disclosure. Although a particular configuration is illustrated here, there are many different configurations of hardware platforms, and this embodiment is intended to represent the class of hardware platforms that may provide a computing device. Furthermore, the designation of this embodiment as a "hardware platform" is not intended to require that all embodiments provide all elements in hardware. Some of the elements disclosed herein may be provided, in various embodiments, as hardware, software, firmware, microcode, microcode instructions, hardware instructions, hardware or software accelerators, or similar. Depending on the embodiment, elements of hardware platform 700 may be omitted, and other elements may be included.

Hardware platform 700 is configured to provide a computing device (e.g., a smartphone, a kiosk, a computer, etc.). In various embodiments, a "computing device" may be or comprise, by way of nonlimiting example, any type of computer, system on a chip (SoC), workstation, server, mainframe, virtual machine (whether emulated or on a "bare metal" hypervisor), network appliance, container, IoT device, high performance computing (HPC) environment, a data center, a communications service provider infrastructure (e.g., one or more portions of an Evolved Packet Core), an in-memory computing environment, a computing system of a vehicle (e.g., an automobile or airplane), an industrial control system, embedded computer, embedded controller, embedded sensor, personal digital assistant, laptop computer, cellular telephone, internet protocol (IP) telephone, smart phone, tablet computer, convertible tablet computer, computing appliance, receiver, wearable computer, handheld calculator, or any other electronic, microelectronic, or microelectromechanical device for processing and communicating data. At least some of the methods and systems disclosed in this specification may be embodied by or conducted on a computing device.

In the illustrated example, hardware platform 700 is arranged in a point-to-point (PtP) configuration. This PtP configuration is popular for personal computer (PC) and server-type devices, although it is not so limited, and any other bus type may be used. The PtP configuration may be an internal device bus that is separate from CAN bus 170 of FIG. 1, although in some embodiments they may interconnect with one another.

Hardware platform 700 is an example of a platform that may be used to implement embodiments of the teachings of this specification. For example, instructions could be stored in storage 750. Instructions could also be transmitted to the hardware platform in an ethereal form, such as via a network interface, or retrieved from another source via any suitable interconnect. Once received (from any source), the instructions may be loaded into memory 704, and may then be executed by one or more processor 702 to provide elements such as an OS 706, operational agents 708, or data 712.

Hardware platform 700 may include several processors 702. For simplicity and clarity, only processors PROC0 702-1 and PROC1 702-2 are shown. Additional processors (such as 2, 4, 8, 16, 24, 32, 64, or 128 processors) may be provided as necessary, while in other embodiments, only one processor may be provided. Processors may have any number of cores, such as 1, 2, 4, 8, 16, 24, 32, 64, or 128 cores.

Processors 702 may be any type of processor and may communicatively couple to chipset 716 via, for example, PtP interfaces. Chipset 716 may also exchange data with other elements. In alternative embodiments, any, or all of the PtP links illustrated in FIG. 7 could be implemented as any type of bus, or other configuration rather than a PtP link. In various embodiments, chipset 716 may reside on the same die or package as a processor 702 or on one or more different dies or packages. Each chipset may support any suitable number of processors 702. A chipset 716 (which may be a chipset, uncore, Northbridge, Southbridge, or other suitable logic and circuitry) may also include one or more controllers to couple other components to one or more central processor units (CPU).

Two memories, 704-1 and 704-2 are shown, connected to PROC0 702-1 and PROC1 702-2, respectively. As an example, each processor is shown connected to its memory in a direct memory access (DMA) configuration, though other memory architectures are possible, including ones in which memory 704 communicates with a processor 702 via a bus. For example, some memories may be connected via a system bus, or in a data center, memory may be accessible in a remote DMA (RDMA) configuration.

Memory 704 may include any form of volatile or nonvolatile memory including, without limitation, magnetic media (e.g., one or more tape drives), optical media, flash, random access memory (RAM), double data rate RAM (DDR RAM) nonvolatile RAM (NVRAM), static RAM (SRAM), dynamic RAM (DRAM), persistent RAM (PRAM), data-centric (DC) persistent memory (e.g., Intel Optane/3D-crosspoint), cache, Layer 1 (L1) or Layer 2 (L2) memory, on-chip memory, registers, virtual memory region, read-only memory (ROM), flash memory, removable media, tape drive, cloud storage, or any other suitable local or remote memory component or components. Memory 704 may be used for short, medium, and/or long-term storage. Memory 704 may store any suitable data or information utilized by platform logic. In some embodiments, memory 704 may also comprise storage for instructions that may be executed by the cores of processors 702 or other processing elements (e.g., logic resident on chipsets 716) to provide functionality.

In certain embodiments, memory 704 may comprise a relatively low-latency volatile main memory, while storage 750 may comprise a relatively higher-latency nonvolatile memory. However, memory 704 and storage 750 need not be physically separate devices, and in some examples may simply represent a logical separation of function (if there is any separation at all). It should also be noted that although DMA is disclosed by way of nonlimiting example, DMA is not the only protocol consistent with this specification, and that other memory architectures are available.

Certain computing devices provide main memory 704 and storage 750, for example, in a single physical memory device, and in other cases, memory 704 and/or storage 750 are functionally distributed across many physical devices. In the case of virtual machines or hypervisors, all or part of a function may be provided in the form of software or firmware running over a virtualization layer to provide the logical function, and resources such as memory, storage, and accelerators may be disaggregated (i.e., located in different physical locations across a data center). In other examples, a device such as a network interface may provide only the minimum hardware interfaces necessary to perform its logical operation and may rely on a software driver to provide additional necessary logic. Thus, each logical block disclosed herein is broadly intended to include one or more logic elements configured and operable for providing the disclosed logical operation of that block. As used throughout this specification, "logic elements" may include hardware, external hardware (digital, analog, or mixed-signal), software, reciprocating software, services, drivers, interfaces, components, modules, algorithms, sensors, components, firmware, hardware instructions, microcode, programmable logic, or objects that may coordinate to achieve a logical operation.

Chipset 716 may be in communication with a bus 728 via an interface circuit. Bus 728 may have one or more devices that communicate over it, such as a bus bridge 732, I/O devices 735, accelerators 746, and communication devices 740, by way of nonlimiting example. In general terms, the elements of hardware platform 700 may be coupled together in any suitable manner. For example, a bus may couple any of the components together. A bus may include any known interconnect, such as a multi-drop bus, a mesh interconnect, a fabric, a ring interconnect, a round-robin protocol, a PtP interconnect, a serial interconnect, a parallel bus, a coherent (e.g., cache coherent) bus, a layered protocol architecture, a differential bus, or a Gunning transceiver logic (GTL) bus, by way of illustrative and nonlimiting example.

Communication devices 740 may broadly include any communication not covered by a network interface and the various I/O devices described herein. Devices may include, for example, various universal serial bus (USB), FireWire, Lightning, or other serial or parallel devices that provide communications. In a particular example, communication device 740 may be used to stream and/or receive data within a CAN. For some use cases, data may be streamed using UDP, which is unidirectional and lacks error correction. UDP may be appropriate for cases where latency and overhead are at a higher premium than error correction. If bi-directional and/or error corrected communication are desired, then a different protocol, such as TCP may be preferred.

I/O devices 735 may be configured to interface with any auxiliary device that connects to hardware platform 700 but that is not necessarily a part of the core architecture of hardware platform 700. A peripheral may be operable to provide extended functionality to hardware platform 700 and may or may not be wholly dependent on hardware platform 700. In some cases, a peripheral may itself be a. Peripherals may include input and output devices such as displays, terminals, printers, keyboards, mice, modems, data ports (e.g., serial, parallel, USB, Firewire, or similar), network controllers, optical media, external storage, sensors, transducers, actuators, controllers, data acquisition buses, cameras, microphones, speakers, or external storage, by way of nonlimiting example.

Bus bridge 732 may be in communication with other devices such as a keyboard/mouse 738 (or other input devices such as a touch screen, trackball, etc.), communication devices 740 (such as modems, network interface devices, peripheral interfaces such as PCI or PCIe, or other types of communication devices that may communicate through a network), and/or accelerators 746. In alternative embodiments, any portions of the bus architectures could be implemented with one or more PtP links.

OS 706 may be, for example, Microsoft Windows, Linux, UNIX, Mac OS X, iOS, MS-DOS, or an embedded or real-time OS (including embedded or real-time flavors of the foregoing). For real-time systems such as an AV, various forms of QNX are popular. In some embodiments, a hardware platform 700 may function as a host platform for one or more guest systems that invoke application (e.g., operational agents 708).

Operational agents 708 may include one or more computing engines that may include one or more non-transitory computer-readable mediums having stored thereon executable instructions operable to instruct a processor to provide operational functions. At an appropriate time, such as upon booting hardware platform 700 or upon a command from OS 706 or a user or security administrator, a processor 702 may retrieve a copy of the operational agent (or software portions thereof) from storage 750 and load it into memory 704.

Processor 702 may then iteratively execute the instructions of operational agents 708 to provide the desired methods or functions.

There are described throughout this specification various engines, modules, agents, servers, or functions. Each of these may include any combination of one or more logic elements of similar or dissimilar species, operable for and configured to perform one or more methods provided by the engine. In some cases, the engine may be or include a special integrated circuit designed to conduct a method or a part thereof, a field-programmable gate array (FPGA) programmed to provide a function, a special hardware or microcode instruction, other programmable logic, and/or software instructions operable to instruct a processor to perform the method. In some cases, the engine may run as a "daemon" process, background process, terminate-and-stay-resident program, a service, system extension, control panel, bootup procedure, basic in/output system (BIOS) subroutine, or any similar program that operates with or without direct user interaction. In certain embodiments, some engines may run with elevated privileges in a "driver space" associated with ring 0, 1, or 2 in a protection ring architecture. The engine may also include other hardware, software, and/or data, including configuration files, registry entries, application programming interfaces (APIs), and interactive or user-mode software by way of nonlimiting example.

In some cases, the function of an engine is described in terms of a "circuit" or "circuitry to" perform a particular function. The terms "circuit" and "circuitry" should be understood to include both the physical circuit, and in the case of a programmable circuit, any instructions or data used to program or configure the circuit.

Where elements of an engine are embodied in software, computer program instructions may be implemented in programming languages, such as an object code, an assembly language, or a high-level language. These languages may be used with any compatible operating systems or operating environments. Hardware elements may be designed manually, or with a hardware description language. The source code may define and use various data structures and communication messages. The source code may be in a computer executable form (e.g., via an interpreter), or the source code may be converted (e.g., via a translator, assembler, or compiler) into a computer executable form, or converted to an intermediate form such as byte code. Where appropriate, any of the foregoing may be used to build or describe appropriate discrete or integrated circuits, whether sequential, combinatorial, state machines, or otherwise.

Communication devices 740 may communicatively couple hardware platform 700 to a wired or wireless network or fabric. A "network," as used throughout this specification, may include any communicative platform operable to exchange data or information within or between computing devices, including any of the protocols discussed in connection with FIGS. 1-3 above. A network interface may include one or more physical ports that may couple to a cable (e.g., an Ethernet cable, other cable, or waveguide), or a wireless transceiver.

In some cases, some, or all of the components of hardware platform 700 may be virtualized, in particular the processor(s) and memory. For example, a virtualized environment may run on OS 706, or OS 706 could be replaced with a hypervisor or virtual machine manager. In this configuration, a virtual machine running on hardware platform 700 may virtualize workloads. A virtual machine in this configuration may perform essentially all the functions of a physical hardware platform.

In a general sense, any suitably configured processor may execute any type of instructions associated with the data to achieve the operations illustrated in this specification. Any of the processors or cores disclosed herein could transform an element or an article (for example, data) from one state or thing to another state or thing. In another example, some activities outlined herein may be implemented with fixed logic or programmable logic (for example, software and/or computer instructions executed by a processor).

Various components of the system depicted in FIG. 7 may be combined in a SoC architecture or in any other suitable configuration. For example, embodiments disclosed herein may be incorporated into systems including mobile devices such as smart cellular telephones, tablet computers, personal digital assistants, portable gaming devices, and similar. These mobile devices may be provided with SoC architectures in at least some embodiments. The SoC (and any other hardware platform disclosed herein) may include analog, digital, and/or mixed-signal, radio frequency (RF), or similar processing elements. Other embodiments may include a multichip module (MCM), with a plurality of chips located within a single electronic package and configured to interact closely with each other through the electronic package. In various other embodiments, the computing functionalities disclosed herein may be implemented in one or more silicon cores in application-specific integrated circuits (ASICs), FPGAs, and other semiconductor chips.

Note that embodiments of the systems 100, 200, and 300 may include one or more distinct interfaces, represented by any suitable network interfaces to facilitate communication via the various networks (including both internal and external networks) described herein. Such network interfaces may be inclusive of multiple wired and/or wireless interfaces (e.g., Wi-Fi, WiMax, 3G, 4G, 5G+, white space, 802.11x, satellite, Bluetooth, LTE, GSM/HSPA, CDMA/EVDO, DSRC, CAN, GPS, etc.). Other interfaces represented by network interfaces 26, may include physical ports (e.g., Ethernet, USB, HDMI, etc.), interfaces for wired and wireless internal subsystems, and the like. Similarly, each of the nodes and user equipment (e.g., mobile devices) of the systems 100, 200, and 300 can also include suitable interfaces for receiving, transmitting, and/or otherwise communicating data or information in a network environment.

The systems 100, 200, and 300 and other associated or integrated components can include one or more memory elements having software and/or hardware for storing information to be used in achieving operations associated with intelligent SOAP report generation, as outlined herein. These devices may further keep information in any suitable memory element (e.g., random access memory (RAM), read only memory (ROM), field programmable gate array (FPGA), erasable programmable read only memory (EPROM), electrically erasable programmable ROM (EEPROM), etc.), software, hardware, or in any other suitable component, device, element, or object where appropriate and based on particular needs. The information being tracked, sent, received, or stored in systems 100, 200, 300 could be provided in any database, register, table, cache, queue, control list, or storage structure, based on particular needs and implementations, all of which could be referenced in any suitable time frame. Any of the memory or storage options discussed herein should be construed as being encompassed within the broad term 'memory element' as used herein in this Specification.

In example embodiments, the operations for intelligent SOAP report generation, as outlined herein, may be implemented by logic encoded in one or more tangible media, which may be inclusive of non-transitory media (e.g., embedded logic provided in an ASIC, digital signal processor (DSP) instructions, software potentially inclusive of object code and source code to be executed by a processor or other similar machine, etc.). In some of these instances, one or more memory elements (e.g., memory) can store data used for the operations described herein. This includes the memory elements being able to store software, logic, code, or processor instructions that are executed to conduct the intelligent SOAP report generation activities described in this Specification.

In the following description, various aspects of the illustrative implementations will be described using terms commonly employed by those skilled in the art to convey the substance of their work to others skilled in the art. However, it will be apparent to those skilled in the art that the embodiments disclosed herein may be practiced with only some of the described aspects. For purposes of explanation, specific numbers, materials, and configurations are set forth in order to provide a thorough understanding of the illustrative implementations. However, it will be apparent to one skilled in the art that the embodiments disclosed herein may be practiced without the specific details. In other instances, well-known features are omitted or simplified in order not to obscure the illustrative implementations.

In the following detailed description, reference is made to the accompanying drawings that form a part hereof wherein numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense. For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C). Reference to "one embodiment" or "an embodiment" in the present disclosure means that a particular feature, structure, or characteristic described in connection with the embodiment is included in at least one embodiment. The appearances of the phrase "in one embodiment" or "in an embodiment" are not necessarily all referring to the same embodiment. The appearances of the phrase "for example," "in an example," or "in some examples" are not necessarily all referring to the same example.

As used herein, the term "when" may be used to indicate the temporal nature of an event. For example, the phrase "event 'A' occurs when event 'B' occurs" is to be interpreted to mean that event A may occur before, during, or after the occurrence of event B, but is nonetheless associated with the occurrence of event B. For example, event A occurs when event B occurs if event A occurs in response to the occurrence of event B or in response to a signal indicating that event B has occurred, is occurring, or will occur. Reference to "one example" or "an example" in the present disclosure means that a particular feature, structure, or characteristic described in connection with the embodiment is included in at least one example or embodiment. The appearances of the phrase "in one example" or "in an example" are not necessarily all referring to the same examples or embodiments. Substantial flexibility is provided by the architecture to enable managing multiple precision time protocol domains in that any suitable arrangements, chronologies, configurations, and timing mechanisms may be provided without departing from the teachings of the present disclosure.

Note that with the examples provided herein, interaction may be described in terms of one, two, three, or more elements. However, this has been done for purposes of clarity and example only. In certain cases, it may be easier to describe one or more of the functionalities by only referencing a limited number of elements. It should be appreciated that the architecture to enable managing multiple precision time protocol domains and its teachings are readily scalable and can accommodate a large number of components, as well as more complicated/sophisticated arrangements and configurations. Accordingly, the examples provided should not limit the scope or inhibit the broad teachings of the architecture to manage multiple precision time protocol domains and as potentially applied to a myriad of other architectures.

It is also important to note that the operations in the preceding flow diagrams illustrate only some of the possible correlating scenarios and patterns that may be executed, some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided in that any suitable arrangements, chronologies, configurations, and timing mechanisms may be provided without departing from the teachings of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. A system that includes an application, configured for:
capturing an audio recording of a patient encounter;
transcribing, by a speech-to-text engine configured to recognize dental terminology including tooth numbering schemes, periodontal charting terms, or orthodontic descriptors, the audio recording into an enhanced text stream;
applying a plurality of prompt modules to the enhanced text stream, each of the prompt modules configured to extract structured information for categories including at least one of: chief complaint, medical history, dental history, periodontal findings, hard tissue findings, radiographic findings, orthodontic conditions, molar relationships, consent, diagnostic tests, assessment, treatment plan, referrals, and patient education;
aggregating outputs of the plurality of prompt modules into a structured record;
ingesting unstructured procedure templates provided by a provider practice;

generating a persistent mapping between each standardized dental procedure code of the Current Dental Terminology (CDT) and a corresponding set of practice-specific procedural steps;
generating, from an aggregated record, a structured SOAP-format dental note in which a plan section is populated with the practice-specific procedural steps associated with one or more CDT codes determined from encountered metadata;
inserting the structured SOAP-format dental note into an electronic dental practice management system (PMS) using an interface configured for the PMS's data model;
analyzing, by an artificial intelligence module, a plurality of historical SOAP-format dental notes for the patient to detect unfinished, deferred, or overlooked treatments;
generating a patient-specific checklist of the treatments; and
presenting the checklist in association with an appointment for the patient.

2. The system of claim 1, wherein the encountered metadata includes data from a previous SOAP report, and data associated with a prevision visit of the patient.

3. The system of claim 1, wherein the enhanced text stream is sent to a large language model (LLM) to automatically create a practitioner-specific SOAP report.

4. The system of claim 1, wherein the structured SOAP-format dental note is structured according to a practitioner's specific requirements.

5. The system of claim 1, wherein the structured SOAP-format dental note is automatically entered into a patient database for subsequent access.

6. The system of claim 1, wherein the enhanced text stream is sent to one or more application program interfaces (APIs) to be provided to an LLM.

7. The system of claim 1, wherein the structured SOAP-format dental note is generated in sections corresponding to API submissions for each respective part of a SOAP protocol.

8. The system of claim 1, wherein the application is further configured for:
aggregating, for patients scheduled in a practice on a given day, a plurality of checklists into an AI-generated daily operational dashboard, the dashboard being configured for segmentation by provider, operatory, discipline, and production value tier; and
displaying the dashboard to a practice team for daily planning.

9. The system of claim 1, wherein superfluous dialogue during an appointment with the patient is automatically minimized in the structured SOAP-format dental note as a result of feedback provided to affect the enhanced text stream.

10. The system of claim 1, further comprising:
providing a subscription model associated with enrolling one or more users that pay a fee to access one or more capabilities of the application.

11. The system of claim 1, further comprising:
providing a claim resolution aspect in the application for one or more services provided to the patient, wherein the claim resolution aspect includes providing access to the structured SOAP-format dental note to an insurance entity.

12. The system of claim 1, wherein the application generates the structured SOAP-format dental note to be affirmed by an associated practitioner before it is published or stored in any database.

13. A product comprising one or more tangible computer-readable non-transitory storage media comprising computer-executable instructions operable to, when executed by at least one computer processor, enable the at least one computer processor to implement operations at a computing device, the operations including:

capturing an audio recording of a patient encounter;

transcribing, by a speech-to-text engine configured to recognize dental terminology including tooth numbering schemes, periodontal charting terms, or orthodontic descriptors, the audio recording into an enhanced text stream;

applying a plurality of prompt modules to the enhanced text stream, each of the prompt modules configured to extract structured information for categories including at least one of: chief complaint, medical history, dental history, periodontal findings, hard tissue findings, radiographic findings, orthodontic conditions, molar relationships, consent, diagnostic tests, assessment, treatment plan, referrals, and patient education;

aggregating outputs of the plurality of prompt modules into a structured record;

ingesting unstructured procedure templates provided by a provider practice;

generating a persistent mapping between each standardized dental procedure code of the Current Dental Terminology (CDT) and a corresponding set of practice-specific procedural steps;

generating, from an aggregated record, a structured SOAP-format dental note in which a plan section is populated with the practice-specific procedural steps associated with one or more CDT codes determined from encountered metadata;

inserting the structured SOAP-format dental note into an electronic dental practice management system (PMS) using an interface configured for the PMS's data model;

analyzing, by an artificial intelligence module, a plurality of historical SOAP-format dental notes for the patient to detect unfinished, deferred, or overlooked treatments;

generating a patient-specific checklist of the treatments; and presenting the checklist in association with an appointment for the patient.

14. The product comprising one or more tangible computer-readable non-transitory storage media of claim 13, wherein the encountered metadata includes data from a previous SOAP report, and data associated with a prevision visit of the patient.

15. The product comprising one or more tangible computer-readable non-transitory storage media of claim 13, wherein the enhanced text stream is sent to a large language model (LLM) to automatically create a practitioner-specific SOAP report.

16. The product comprising one or more tangible computer-readable non-transitory storage media of claim 13, wherein the structured SOAP-format dental note is structured according to a practitioner's specific requirements.

17. The product comprising one or more tangible computer-readable non-transitory storage media of claim 13, wherein the structured SOAP-format dental note is automatically entered into a patient database for subsequent access.

18. The product comprising one or more tangible computer-readable non-transitory storage media of claim 13, wherein the enhanced text stream is sent to one or more application program interfaces (APIs) to be provided to an LLM.

19. The product comprising one or more tangible computer-readable non-transitory storage media of claim 13, wherein the structured SOAP-format dental note is generated in sections corresponding to API submissions for each respective part of a SOAP protocol.

20. The product comprising one or more tangible computer-readable non-transitory storage media of claim 13, wherein superfluous dialogue during an appointment with the patient is automatically minimized in the structured SOAP-format dental note as a result of feedback provided to affect the enhanced text stream.

\* \* \* \* \*